United States Patent
Pikul et al.

(10) Patent No.: US 8,981,114 B2
(45) Date of Patent: Mar. 17, 2015

(54) DERIVATIVES OF 1-(SUBSTITUTED SULFONYL)-2-AMINOIMIDAZOLINE AS ANTITUMOR AND ANTIPROLIFERATIVE AGENTS

(71) Applicant: OncoArendi Therapeutics Sp. z.o.o., Warsaw (PL)

(72) Inventors: Stanislaw Wieslaw Pikul, Jaslo (PL); Wieslaw Marek Cholody, Frederick, MD (US)

(*) Notice: Subject to any disclaimer, the term of this patent is extended or adjusted under 35 U.S.C. 154(b) by 0 days.

(21) Appl. No.: 14/307,272

(22) Filed: Jun. 17, 2014

(65) Prior Publication Data

US 2014/0309259 A1  Oct. 16, 2014

Related U.S. Application Data

(63) Continuation of application No. 14/249,226, filed on Apr. 9, 2014, which is a continuation of application No. PCT/IB2014/060200, filed on Mar. 27, 2014.

(60) Provisional application No. 61/810,276, filed on Apr. 10, 2013.

(30) Foreign Application Priority Data

Apr. 10, 2013  (PL) .................................. 403491

(51) Int. Cl.
| | |
|---|---|
| C07D 233/42 | (2006.01) |
| C07D 403/12 | (2006.01) |
| C07D 405/14 | (2006.01) |
| A61K 31/4178 | (2006.01) |
| A61K 45/06 | (2006.01) |
| C07C 247/06 | (2006.01) |
| C07D 401/14 | (2006.01) |
| A61K 31/454 | (2006.01) |
| C07D 409/14 | (2006.01) |
| C07D 403/14 | (2006.01) |
| A61K 31/506 | (2006.01) |
| A61K 31/4439 | (2006.01) |
| A61K 31/4709 | (2006.01) |

(52) U.S. Cl.
CPC ............ *C07D 403/12* (2013.01); *C07D 405/14* (2013.01); *A61K 31/4178* (2013.01); *A61K 45/06* (2013.01); *C07C 247/06* (2013.01); *C07D 401/14* (2013.01); *A61K 31/454* (2013.01); *C07D 409/14* (2013.01); *C07D 403/14* (2013.01); *A61K 31/506* (2013.01); *A61K 31/4439* (2013.01); *A61K 31/4709* (2013.01)
USPC ........................................................ 548/347.1

(58) Field of Classification Search
CPC ................................................... C07D 233/42
USPC ................................................... 548/347.1
See application file for complete search history.

(56) References Cited

U.S. PATENT DOCUMENTS

| | | | |
|---|---|---|---|
| 3,538,085 A | * | 11/1970 | Dietrich ...................... 548/331.1 |
| 5,929,103 A | | 7/1999 | Yoon et al. |
| 5,932,742 A | | 8/1999 | Yoon et al. |
| 6,184,242 B1 | | 2/2001 | Bley et al. |
| 2004/0019092 A1 | | 1/2004 | Berney et al. |

FOREIGN PATENT DOCUMENTS

| | | |
|---|---|---|
| CS | 97860 B5 | 12/1960 |
| EP | 0 432 442 A1 | 6/1991 |
| GB | 1174152 A | 12/1969 |
| WO | 98/07719 A1 | 2/1998 |

OTHER PUBLICATIONS

Dietrich, Nov. 1970, CAPlus Doc No. 72:12718.*
Bundgaard, Design of Prodrugs, 1985, Elsevier, Chapter 1, p. 1-4.*
Han, targeted Prodrug Design to Optimize Drug Delivery, 2000, AAPS Pharmsci, vol. 2 (1), p. 1-11.*
International Search Report and Written Opinion mailed Jul. 3, 2014, for International Application No. PCT/IB2014/060200, 9 pages.
Jung et al., "Synthesis and Evaluation of Cytotoxic Activity of Novel Arylsulfonylimidazolidinones," *Bioorganic & Medicinal Chemistry Letters* 6(21):2553-2558, 1996.
Polish Search Report, dated Nov. 12, 2013, for Polish Application No. P.403491, 3 pages.

* cited by examiner

*Primary Examiner* — Rebecca Anderson
*Assistant Examiner* — Karen Cheng
(74) *Attorney, Agent, or Firm* — Seed IP Law Group PLLC

(57) ABSTRACT

The invention provides novel, water-soluble 2-aminoimidazoline derivatives having general Formula (I) as well as some precursors of Formula (I), which are very potent inducers of G2/M cell cycle arrest. In treated tumor cells, compounds of Formula (I) give gene expression profile distinct from known antimitotic agents. The invention also provides methods for preparing the compounds, and methods of using the compounds for the treatment of cancer or other mammalian diseases characterized by undesirably high levels of cell proliferation. The compounds of the invention are also expected to have utility as research tools.

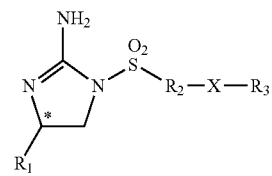

Formula I

15 Claims, No Drawings

DERIVATIVES OF 1-(SUBSTITUTED SULFONYL)-2-AMINOIMIDAZOLINE AS ANTITUMOR AND ANTIPROLIFERATIVE AGENTS

CROSS-REFERENCE TO RELATED APPLICATIONS

This application is a continuation of U.S. patent application Ser. No. 14/249,226, filed Apr. 9, 2014, which is a continuation of International Patent Application PCT/IB2014/060200, accorded an international filing date of Mar. 27, 2014, which claims priority to Polish Application No. PL403491 filed Apr. 10, 2013 and to U.S. Provisional Application No. 61/810,276, filed Apr. 10, 2013. All of the prior applications are incorporated herein by reference in their entireties.

FIELD OF THE INVENTION

This invention relates to novel compounds that posses antineoplastic activity. In particular, the present invention relates to novel derivatives of 2-aminoimidazoline having various sulfonyl substituents at position 1 and alkyl or aryl substituents at position 4, their tautomers, pharmaceutically acceptable salts, hydrates, solvates, and prodrugs, processes for their preparation, their use as antitumor drugs and pharmaceutical compositions containing them as active ingredients.

BACKGROUND OF THE INVENTION

The cell cycle is an ordered set of events, culminating in cell growth and division into two daughter cells. It consists of four distinct stages: gap number 1 (G1); synthesis (S); gap number 2 (G2) and mitosis or cell division (M). Control of the cell cycle is very complex and involves regulation at a number of levels. Cell cycle checkpoints are regulatory pathways that control the order and timing of cell cycle transitions and ensure that critical events such as DNA replication and chromosome segregation are completed correctly before letting the cell progress further through the cycle.

In cancerous cells, the normal regulatory processes are disrupted and cell growth is uncontrolled. One of the main abnormalities in human cancer cells is the loss of the G1 phase checkpoint, primarily due to mutations in p53. Consequently, enforcement of the G2/M checkpoint represents an attractive mode of action for new antineoplastic agents, as sustained arrest of cancer cells in G2/M phase triggers cell death by apoptosis.

G2/M progression is tightly regulated by several cellular macromolecules, including tubulins, microtubule-associated proteins and motor proteins, such as kinesins and dyneins. Targeting the G2/M checkpoint has been clinically validated with drugs that either stabilize (taxanes) or disrupt (vinca alkaloids) microtubule formation. In addition, the importance of G2/M arrest was also validated in the clinic with drugs that have different molecular targets, e.g., Velcade (proteasome inhibitor).

We describe here a new class of water-soluble, highly potent compounds that are able to arrest tumor cells in G2/M phase but producing gene expression profile different from known antimitotic agents. It is possible that treatment of solid tumor cancers with such drugs may lead to higher anticancer efficacy and reduced toxic side effects typical for antimitotic agents. These compounds are derived from 1-(substituted sulfonyl)-2-aminoimidazoline. Structurally related 1-sulphanilyl-2-imino-imidazolidine derivatives have been reported as anti-glycemic agents (see, for example, GB Patent No. 1174152), and arylsulfonylimidazolone derivatives were disclosed as antineoplastic agents, with activity superior to the known antitumor sulfonylureas (U.S. Pat. No. 5,932,742). However, those compounds are not soluble in water, which is a serious disadvantage for cytotoxic anticancer agents that commonly are administered in highly controlled manner as slow iv injections.

DETAILED DESCRIPTION OF THE INVENTION

This invention provides a new class of 2-aminoimidazoline derivatives containing substituted sulfonyl moiety attached to the nitrogen at position 1 and aliphatic or aromatic substituent attached to the carbon at position 4, and their use as antineoplastic agents. The compounds of the invention have a general structure presented in Formula (I),

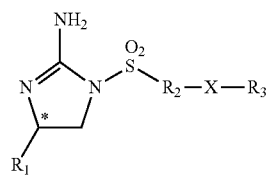

Formula I in which:
$R_1$ is
(a) a hydrogen atom;
(b) a substituted or unsubstituted alkyl, preferentially as S stereoisomer;
(c) a substituted or unsubstituted aryl or heteroaryl, preferentially as S stereoisomer;
$R_2$ is
(a) a substituted or unsubstituted alkyl;
(b) a substituted or unsubstituted phenyl;
(c) a 5- or 6-membered, optionally substituted saturated or unsaturated heterocyclic group having from one to three heteroatoms selected from nitrogen, oxygen and sulfur;
(d) a saturated or unsaturated fused ring carbocyclic group having from 8 to 10 ring atoms; or preferentially
(e) a heterocyclic moiety having more than 6 carbon atoms and one or more nitrogen, sulfur and/or oxygen atoms. The moieties may contain the atoms in a single ring or in fused rings and can be saturated or unsaturated and additionally substituted with amino or carboxy groups. Examples of such heterocyclic moieties include indolyl, quinolyl, chromanyl, benzimidazolyl, benzoxazolyl, benzothienyl, benzofuranyl, and quinolinyl.
X is a hydrogen atom, carbonyl, thiocarbonyl or imine.
If X is a hydrogen atom then $R_3$ is null.
If X is not hydrogen then $R_3$ is:
(a) a substituted or unsubstituted linear, branched or cyclic alkyl which additionally can be connected to an aromatic or heterocyclic moiety,
(b) a substituted or unsubstituted phenyl,
(c) a 5- or 6-membered, optionally substituted saturated or unsaturated heterocyclic group having from one to three heteroatoms selected from nitrogen, oxygen and sulfur;
(d) $NR'(CH_2)_nR''$ where
R' is hydrogen or alkyl,
n is 0-3,
R'' is unsubstituted or substituted alkyl, cycloalkyl, phenyl, benzyl, a 5- or 6-membered, optionally substituted saturated or unsaturated heterocyclic group having from one to three heteroatoms selected from nitrogen, oxygen and sulfur, and R' and R" can be connected or not;

(e) O(CH$_2$)$_n$R" or S(CH$_2$)$_n$R" where R" and n are as defined above.

The invention also encompasses tautomers, pharmaceutically acceptable salts, hydrates, solvates, and prodrugs of the above-defined compounds of Formula (I).

The term "halo", as used herein, unless otherwise indicated, includes fluoro, chloro, bromo or iodo. Preferred halo groups are fluoro, chloro and bromo.

The term "alkyl" as used herein is intended to include straight chain, branched and cyclic alkyl groups, being saturated monovalent hydrocarbon radicals. As used herein, the straight alkyl may have 1-20, preferably 1-10, more preferably 1-7 carbon atoms. The branched and cyclic alkyls may have 3-20, preferably 3-10, more preferably 3-7 carbon atoms. Lower alkyl denotes alkyl having up to 7 carbon atoms.

The term "alkenyl", as used herein, unless otherwise indicated, includes monovalent hydrocarbon radicals having at least one carbon-carbon double bond and also having straight, cyclic or branched moieties as provided above in the definition of "alkyl". As used herein, alkenyl may have 2-20, preferably 2-10, more preferably 2-7, carbon atoms.

The term "alkynyl", as used herein, unless otherwise indicated, includes monovalent hydrocarbon radicals having at least one carbon-carbon triple bond and also having straight, cyclic or branched moieties as provided above in the definition of "alkyl". As used herein, alkynyl may have 2-20, preferably 2-10, more preferably 2-6, carbon atoms.

The term "alkoxy", as used herein, unless otherwise indicated, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl. As used herein, aryl may have 6-18, preferably 6-12, more preferably 6-10, ring carbon atoms.

The term "4-10 membered heterocyclic", as used herein, unless otherwise indicated, includes aromatic and non-aromatic heterocyclic groups containing one or more heteroatoms each selected from O, S and N, wherein each heterocyclic group has from 4-10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo [3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached). As used herein, heterocyclic groups may have up to 20 atoms in their ring systems.

The phrase "pharmaceutically acceptable salt(s)", as used herein, unless otherwise indicated, includes salts of acidic or basic groups, which may be present in the compounds of Formula (I).

The compounds of Formula (I) that are basic in nature are capable of forming a wide variety of salts with various inorganic and organic acids. The acids that may be used to prepare pharmaceutical acceptable acid addition salts of such basic compounds of Formula (I) are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (4,4'-methylenebis(3-hydroxy-2-naphthoate)) salts.

Those compounds of the Formula (I) that are acidic in nature are capable of forming base salts with various pharmacologically acceptable cations. Examples of such salts include the alkali metal or alkaline earth metal salts and, particularly, the sodium and potassium salts, and also organic amine as well as ammonium salts.

Certain compounds of Formula (I) may have asymmetric centers and therefore exist in different enantiomeric forms. This invention relates to the use of all optical isomers and stereoisomers of the compounds of Formula (I) and mixtures thereof. The compounds of Formula (I) may also exist as tautomers. This invention relates to the use of all such tautomers and mixtures thereof.

The subject invention also includes isotopically-labelled compounds, and the pharmaceutically acceptable salts thereof, which are identical to those recited in Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula (I) of this invention and prodrugs thereof can generally be prepared by carrying out the procedures disclosed in the Schemes and/or in the Examples and Preparations below, by substituting a readily available isotopically labelled reagent for a non-isotopically labelled reagent.

Compounds of Formula (I) having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula (I). The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionin sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, *Advanced Drug Delivery Reviews* (1996) 19, 115. Carbamate prodrugs of hydroxy and amino groups are also included, as are carbonate prodrugs and sulfate esters of hydroxy groups. Derivatization of hydroxy groups as (acyloxy) methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., *J. Medicinal Chemistry* (1996) 39, 10.

By the methods provided herein, and by obvious modifications thereto, the compounds of this invention may be prepared from the appropriate starting materials. It is intended that where optical isomers are available, the pure isomers and diastereoisomers, and any and all mixtures thereof, be within the scope of the claims. The exemplified compounds, and the methods for their preparation, are presented merely by way of example, and the presentation of selected examples is not intended to limit the scope of the invention.

The preferred general method for the synthesis of compounds of Formula (I) is presented in Scheme 1. In this procedure, a desired 1-substituted-1-tert-butoxycarbonylamino-2-azidoethane 1, synthesized by a slightly modified method described earlier in EP 0432442, is hydrogenated in dichloromethane or THF using 10% Pd/C to a corresponding amine which, without isolation, is condensed with a suitable sulfonyl chloride to give sulfonamide 2. Compounds 2 are then transformed into cyanosulfonamides 3 by reaction with cyanogen bromide at −30° C. in the presence of triethylamine. Under those conditions the attachment of the cyano group occurs only on the sulfonamide nitrogen atom. When heated in boiling THF or MeOH in the presence of a base, for example triethylamine, compounds 3 undergo cyclization to 2-iminoimidazolidines 4, which then can be deprotected with trifluoroacetic acid in dichloromethane to give the desired 2-aminoimidazoline derivatives 5 (Formula I). Compounds 3 can also be converted in one-step into 5 by treatment with trifluoroacetic acid in DCM.

We found that compounds 3 and 4 are rapidly transformed into 5 in mouse blood serum, as well as when the compounds are administered to laboratory animals. Because of this, we consider both compounds 3 and 4 as prodrugs of the compounds of Formula (I).

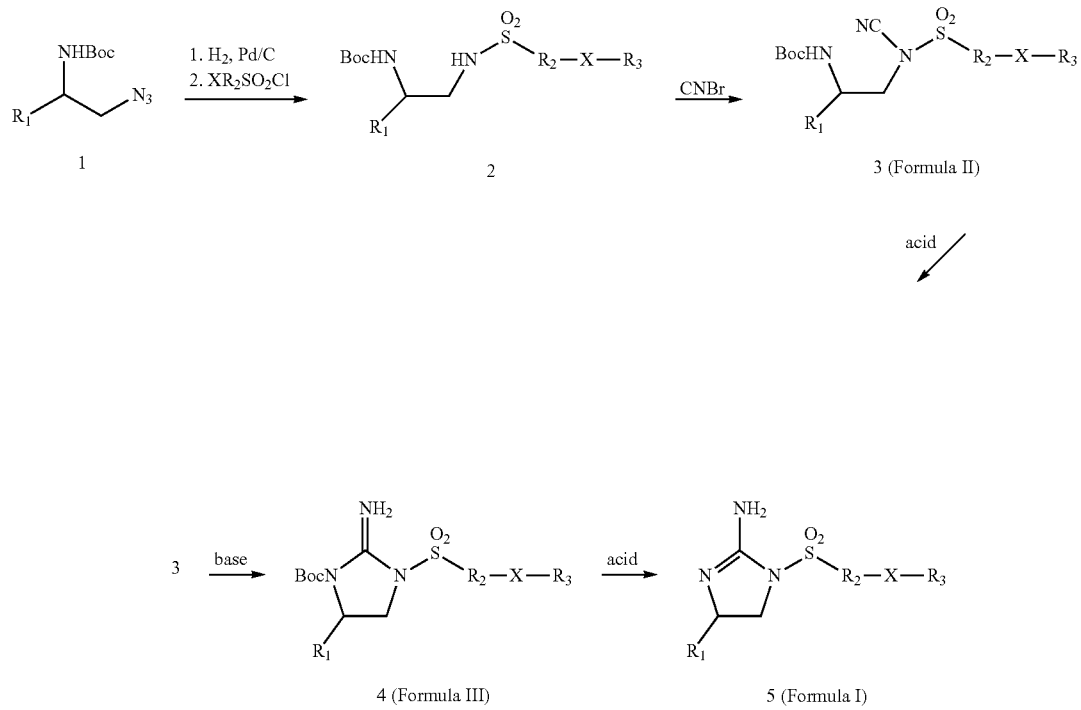

Scheme 1.

In a particularly preferred embodiment of this invention, R₂ in Formula (I) represents a heterocyclic system, especially indoline, to which additional substituent R₃ is connected through the carbonyl group. The most convenient synthetic pathway for the synthesis of such compounds is presented in Scheme 2, and by analogy it can be easily applied to systems other than indoline.

Another areas of use of compounds of this invention are disorders associated with lymphocyte proliferation in organ transplantation, inflammatory, allergic or autoimmune disease selected from the group of asthma, psoriasis, rheumatoid arthritis, inflammatory bowel diseases, systemic lupus erythromatosus, vasculitis, vascular hyperproliferation, diabetic retinopathy, liver cirrhosis, and gout.

Scheme 2.

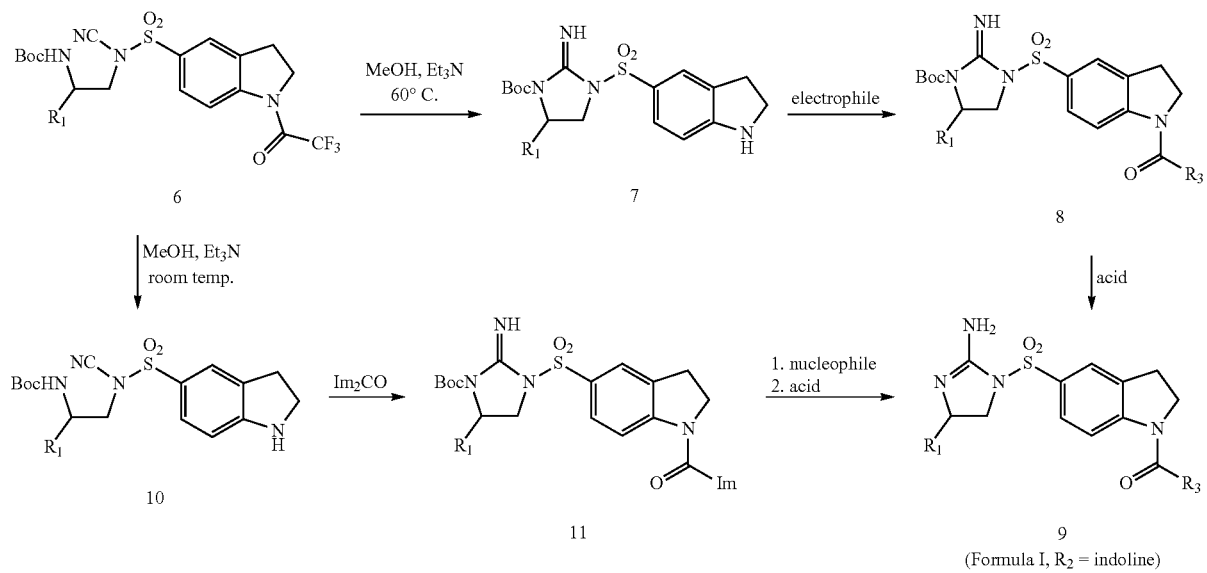

Compound 6 is obtained as described in Scheme 1. Hydrolysis of the trifluoroacetamid group accompanied by closure of the imidazolidine ring provides unprotected indoline 7 which could be functionalized by reacting with variety of electrophiles, for example, acid chlorides, anhydrides, isocyanates and thioisocyanates to give compound 8. Removal of Boc protection leads to the target compound 9. Alternatively, a mild hydrolysis of compound 6 provides deprotected intermediate 10, which is than transformed into 11 by reaction with carbonyl diimidazole. The activated intermediate 10 undergoes reaction with a variety of nucleophiles, for example amines, alcohols, thiols, etc. which, following removal of the Boc protection, lead to compounds 8 (Formula I).

Another object of this invention is to provide a method of treating a mammal suffering from cancer or another disease characterized by undesirable cell proliferation, with the compounds of the invention. The method of the invention comprises administering to an individual mammal a therapeutically effective amount of at least one compound of Formula (I) or a prodrug or pharmaceutically acceptable salt thereof, which is sufficient to inhibit the undesired cell proliferation or tumor growth.

A preferred use of compounds of this invention is to treat disorders selected from breast, colorectal, lung, prostate, bladder, brain, head and neck, renal, kidney, squamous cell, esophageal, gastric, thyroid, pancreatic, skin, bone, liver, ovarian and gynecological cancer, sarcomas, melanoma and hematological malignancies (acute and chronic lymphocytic and myelogenous lekemias, Hodgkin and non-Hodgkin lymphomas, mycosis fungoides, Sézary syndrome), and pre-malignant diseases (lymphoproliferative disorders).

The dose of the compound used in the treatment of such disease will vary in the usual way with the weight and metabolic health of the patient, the severity of any side effects, and the relative efficacy of the compound employed when used against the type of tumor involved. The preferred initial dose for the general patient population will be determined by routine dose-ranging studies, as is conducted for example during clinical studies. Therapeutically effective doses for individual patients may be determined by titrating the amount of drug given to the individual to arrive at the desired therapeutic effect without incurring an unacceptable level of side effects, as is currently and routinely done with other forms of chemotherapy.

Administration of the compounds of this invention may be by any method used for administering therapeutics, such as for example oral, intravenous, intramuscular, subcutaneous, or rectal administration.

This invention also provides pharmaceutical compositions useful for providing anti-proliferative including anti-tumor activity, which comprise at least one compound of the invention. In addition to comprising at least one of the compounds described herein, or a pharmaceutically acceptable addition salt or prodrug thereof, the pharmaceutical composition may also comprise additives such as preservatives, excipients, fillers, wetting agents, binders, disintegrants, buffers, and/or carriers. There exist a wide variety of pharmaceutically acceptable additives for pharmaceutical dosage forms, and selection of appropriate additives is a routine matter for those skilled in art of pharmaceutical formulation.

The composition may be in the form of tablets, capsules, powders, granules, suppositories, reconstitutable powders, or liquid preparations such as oral or sterile parenteral solutions or suspensions. For administration by injection and/or infusion, the compositions or formulations according to the invention may be dissolved or suspended as known in the art in a vehicle suitable for injection or infusion. Such vehicles include isotonic saline, buffered or unbuffered, D5W, and the like. They also may contain other ingredients, including other active ingredients.

The composition may also be in the form of controlled release or sustained release compositions as known in the art, for instance, in matrices of biodegradable or non-biodegradable injectable polymeric microspheres or microcapsules, in liposomes, in emulsions, and the like.

The novel compounds of this invention may be used per se (free base), or in the form of their pharmaceutically acceptable, water-soluble addition salts, such as hydrochlorides, hydrobromides, acetates, sulfates, methanesulfonates, citrates, and the like.

The present invention is illustrated by the following Examples.

EXAMPLE 1

Preparation of
(S)-2-phenyl-2-tert-butoxycarbonylaminoethylazide
(1, $R_1$=Ph)

(S)-2-Phenyl-2-tert-butoxycarbonylaminoethyl methanesulfonate (15.77 g, 0.05 mol) was dissolved in 50 mL DMF followed by the addition of sodium azide (19.5 g, 0.3 mol). The mixture was stirred for 24 hrs at 55° C., cooled to room temperature, poured into cold water (500 mL) and stirred vigorously for 20 minutes. Precipitate was collected by filtration, washed with water and dried, affording 9.97 g of the title compound as a white solid. Yield: 76%; $(MH)^+$=263; $^1$H NMR (DMSO-$d_6$): 1.37 (s, 9H), 3.36-3.50 (m, 2H), 4.69-4.75 (m, 1H), 7.23-7.36 (m, 5H), 7.65-7.68 (d, J=9.2 Hz, 1H).

EXAMPLE 2

Preparation of (S)-1-phenyl-1-(tert-butoxycarbonylamino)-2-(1-trifluoroacetylindoline-5-sulfonyl)aminoethane (2, $R_1$=Ph, $R_2$X=(1-trifluoroacetylindolin)-5-yl)

A mixture of (S)-2-phenyl-2-tent-butoxycarbonylaminoethylazide (10.50 g, 0.04 mol) dissolved in 250 mL dichloromethane and 2.5 g of 10% Pd/C was hydrogenated for 5 hrs at 70 psi of $H_2$. The catalyst was separated by filtration. To the filtrate triethylamine (8 mL) was added, the mixture was cooled to −20° C. followed by slow addition of 1-(trifluoroacetyl)indoline-5-sulfonyl chloride (12.56 g, 0.04 mol) dissolved in 150 mL dichloromethane. The reaction mixture was then stirred overnight at room temperature. Water (500 mL) was added and the mixture was shaken well, organic layer was separated, shaken with 200 mL 2% citric acid, separated and dried with $MgSO_4$. The drying agent was separated by filtration. The filtrate was concentrated and the title product was precipitated by addition of hexane. Yield: 17.67 g, (86%); $(MH)^+$=514; $^1$H NMR (DMSO-$d_6$): 1.33 (s, 9H), 2.85-2.99 (m, 2H), 3.26-3.30 (t, J=8.0 Hz, 2H), 4.31-4.35 (t, J=8.0 Hz, 2H), 4.53-4.59 (m, 1H), 7.19-7.35 (m, 6H), 7.66-7.68 (m, 2H), 7.72-7.75 (t, J=6.0 Hz, 1H), 8.13-8.15 (d, J=8.8 Hz, 1H).

EXAMPLE 3

Preparation of (S)-1-phenyl-1-(tert-butoxycarbonylamino)-2-N-cyano-N-(1-trifluoroacetylindoline-5-sulfonyl)aminoethane (6, $R_1$=Ph)

A solution of (S)-1-phenyl-1-(tert-butoxycarbonylamino)-2-(1-trifluoroacetyl-indoline-5-sulfonyl)aminoethane (10.27 g, 0.02 mol) in dichloromethane (400 mL) and triethylamine (40 mL) was cooled to −50° C. followed by the addition of 3M solution of cyanogen bromide in dichloroethane (30 mL) under well ventilated hood (!). The reaction mixture was stirred at −30° C. for 30 minutes. The reaction was removed from the cooling bath, water (500 mL) was added in one portion and the mixture was stirred for 10 minutes. The water layer was adjusted to pH~7 by the addition of 10% citric acid and shaken well. The organic layer was separated, dried with $MgSO_4$ and condensed. A jelly-like product was formed after the addition of ether. The product was filtered, washed with ether and dried. Yield: 9.17 g (85%); $(MH)^+$=539; $^1$H NMR (DMSO-$d_6$): 1.34 (s, 9H), 2.98-3.02 (t, J=8.8 Hz, 2H), 3.48-3.62 (m, 4H), 4.67-4.73 (m, 1H), 6.49-6.51 (d, J=8.4 Hz, 1H), 7.01 (s, 1H), 7.24-7.33 (m, 6H), 7.41-7.44 (dd, J=2.0 Hz, J=8.4 Hz, 1H), 7.59-7.62 (d, J=9.6 Hz, 1H).

EXAMPLE 4

Preparation of (S)-4-phenyl-1-(indoline-5-sulfonyl)-3-tert-butoxycarbonyl-4,5-dihydro-1H-imidazol-2-imine (7, $R_1$=Ph)

(S)-1-Phenyl-1-(tert-butoxycarbonylamino)-2-N-cyano-N-(1-trifluoroacetylindoline-5-sulfonyl)aminoethane (8.08 g, 0.015 mol) was suspended in methanol (100 mL) and triethylamine (10 mL) and stirred overnight at 60° C. Water (200 mL) was added to the reaction mixture, and methanol was evaporated. White precipitate was collected by filtration, dried, and crystallized from dichloromethane and hexane to give 5.78 g of the title compound. Yield: 87%; $(MH)^+$=443

EXAMPLE 5

Preparation of (S)-4-phenyl-1-((N-1-methyl-1H-pyrrol-2-yloyl)indoline-5-sulfonyl)-3-tert-butoxycarbonyl-4,5-dihydro-1H-imidazol-2-imine (8, $R_1$=Ph, $R_3$=1-methyl-1H-pyrrol-2-yl)

To a solution of (S)-4-phenyl-1-(indoline-5-sulfonyl)-3-tert-butoxycarbonyl-4,5-dihydro-1H-imidazol-2-imine (1.33 g, 0.003 mol) in dichloromethane (25 mL) and triethylamine (0.75 mL) cooled to −20° C. was added commercially available 95% pure 1-methyl-1H-pyrrole-2-carbonyl chloride (0.5 g, 0033 mol) dissolved in dichloromethane (5 mL). The reaction mixture was stirred overnight at room temperature. Water (50 mL) was added, shaken well, pH was adjusted with 10% citric acid to ~5. Organic layer was separated, dried and evaporated. Crude material was crystallized from dichloromethane-hexane to give 1.27 g of the title compound. Yield: 77%; $(MH)^+$=550.

EXAMPLES 6-33

The following compounds are made using the methods described and exemplified above. All compounds presented in the table below provided NMR spectra consistent with their structures, and correct parent ion signals corresponding to their molecular weights when characterized by mass spectrometry run in the ESI mode. In some cases the predominant ion had a mass of one hunderd dalton lower due to the loss of the Boc group during the mass spectrometry test.

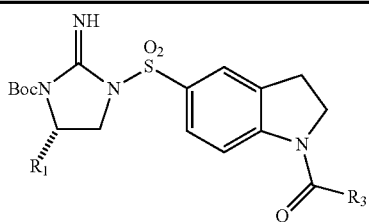

| Example | R₁ | R₃ |
|---------|-----|-----|
| 6 | Ph | 2-furan |
| 7 | Ph | 2-thiophene |
| 8 | Ph | CH₃ |
| 9 | Ph | C₂H₅ |
| 10 | Ph | n-C₃H₇ |
| 11 | Ph | iso-C₃H₇ |
| 12 | Ph | CH₂-(2-thiophene) |
| 13 | Ph | Ph |
| 14 | Ph | p-C₆H₄NO₂ |
| 15 | Ph | p-C₆H₄N(CH₃)₂ |
| 16 | Ph | p-C₆H₄OC₂H₅ |
| 17 | Ph | CH₂Ph |
| 18 | Ph | OCH₃ |
| 19 | Ph | ![piperidine-acetyl] |
| 20 | Ph | cyclohexyl |
| 21 | Ph | 1-naphthyl |
| 22 | 4-F—C₆H₄— | 2-furan |
| 23 | 4-F—C₆H₄— | 2-N-methylpyrrole |
| 24 | 2,4-F₂—C₆H₃— | 2-N-methylpyrrole |
| 25 | 4-Cl—C₆H₄ | 2-N-methylpyrrole |
| 26 | 4-CH₃O—C₆H₄— | 2-N-methylpyrrole |
| 27 | 3-Cl—C₆H₄— | 2-N-methylpyrrole |
| 28 | 2-Cl—C₆H₄— | 2-N-methylpyrrole |
| 29 | 3-Me—C₆H₄— | 2-N-methylpyrrole |
| 30 | 2-Me—C₆H₄— | 2-N-methylpyrrole |
| 31 | CH₃— | 2-N-methylpyrrole |
| 32 | 3,5-Cl₂—C₆H₃— | 2-N-methylpyrrole |
| 33 | 2-pyrimidine | 2-N-methylpyrrole |

EXAMPLE 34

Preparation of (S)-4-phenyl-1-((N-1-methyl-1H-pyrrol-2-yloyl)indoline-5-sulfonyl)-4,5-dihydro-1H-imidazol-2-amine (9, R₁=Ph, R₃=1-methyl-1H-pyrrol-2-yl)

(S)-4-Phenyl-1-((N-1-methyl-1H-pyrrol-2-yloyl)indoline-5-sulfonyl)-3-tert-butoxycarbonyl-4,5-dihydro-1H-imidazol-2-imine from Example 6 (1.10 g; 0.002 mol) was suspended in dichloromethane and thianisole (0.4 mL) was added with stirring followed by the addition of trifluoroacetic acid (4 mL). Stirring was continued until no more starting material was detected by HPLC (about 5-6 hrs). Reaction mixture was diluted with dichloromethane (20 mL) and 2 mL of 2N solution of HCl in ether was added. Product was precipitated as a salt by the addition of ether (100 mL). The precipitate was collected by filtration, washed with ether and dried. Crude material was dissolved in methanol-water, and poured with stirring into 1N sodium hydroxide water solution. White precipitate of product as free base was collected by filtration, washed with water and dried affording 503 mg. Yield: 56%; (MH)⁺=450; ¹H NMR (DMSO-d₆): 3.12 (m, 2H), 3.26 (m, 1H), 3.78 (s, 3H), 4.10 (t, 1H), 4.37 (m, 2H), 4.74 (m, 1H), 6.12 (m, 1H), 6.38 (br s, 2H ex), 6.78 (m, 1H), 6.98 (m, 2H), 7.05 (m, 1H), 7.19 (m, 3H), 7.74 (m, 2H), 8.01 (d, 1H).

EXAMPLES 35-70

The following compounds are made using the methods described and exemplified above. All compounds presented in the table below provided NMR spectra consistent with their structures, and correct parent ion signals corresponding to their molecular weights when characterized by mass spectrometry run in the ESI mode.

| Example | R₁ | R₃ | R₄ | n | X |
|---------|-----|-----|-----|---|----|
| 35 | Ph | 2-furan | H | 1 | C=O |
| 36 | iso-C₃H₇ | 2-furan | H | 1 | C=O |
| 37 | cyclohexyl | 2-furan | H | 1 | C=O |
| 38 | Ph | 2-thiophene | H | 1 | C=O |
| 39 | Ph | CH₃ | H | 1 | C=O |
| 40 | Ph | C₂H₅ | H | 1 | C=O |
| 41 | Ph | n-C₃H₇ | H | 1 | C=O |
| 42 | Ph | iso-C₃H₇ | H | 1 | C=O |
| 43 | Ph | CH₂-(2-thiophene) | H | 1 | C=O |
| 44 | Ph | Ph | H | 1 | C=O |
| 45 | Ph | p-C₆H₄NO₂ | H | 1 | C=O |
| 46 | Ph | p-C₆H₄N(CH₃)₂ | H | 1 | C=O |
| 47 | Ph | p-C₆H₄OC₂H₅ | H | 1 | C=O |
| 48 | Ph | CH₂Ph | H | 1 | C=O |
| 49 | Ph | OCH₃ | H | 1 | C=O |
| 50 | Ph | ![piperidine-acetyl] | H | 1 | C=O |
| 51 | Ph | cyclohexyl | H | 1 | C=O |
| 52 | Ph | 1-naphthyl | H | 1 | C=O |
| 53 | Ph | 3-pyridine | H | 1 | C=O |
| 54 | Ph | p-NH₂—C₆H₄ | Me | 1 | C=O |
| 55 | Ph | iso-C₃H₇NH | H | 1 | C=S |
| 56 | Ph | n-C₃H₇ | H | 2 | C=O |
| 57 | Ph* | n-C₃H₇ | H | 1 | C=O |
| 58 | 4-F—C₆H₄— | 2-furan | H | 1 | C=O |
| 59 | 4-F—C₆H₄— | 2-N-methylpyrrole | H | 1 | C=O |
| 60 | 2,4-F₂—C₆H₃— | 2-N-methylpyrrole | H | 1 | C=O |
| 61 | 4-Cl—C₆H₄ | 2-N-methylpyrrole | H | 1 | C=O |
| 62 | 4-CH₃O—C₆H₄— | 2-N-methylpyrrole | H | 1 | C=O |
| 63 | 3-Cl—C₆H₄— | 2-N-methylpyrrole | H | 1 | C=O |
| 64 | 2-Cl—C₆H₄— | 2-N-methylpyrrole | H | 1 | C=O |
| 65 | 3-Me—C₆H₄— | 2-N-methylpyrrole | H | 1 | C=O |
| 66 | 2-Me—C₆H₄— | 2-N-methylpyrrole | H | 1 | C=O |
| 67 | CH₃— | 2-N-methylpyrrole | H | 1 | C=O |
| 68 | 3,5-Cl₂—C₆H₃— | 2-N-methylpyrrole | H | 1 | C=O |
| 69 | 2-pyrimidine | 2-N-methylpyrrole | H | 1 | C=O |
| 70 | Ph | — | H | 1 | H |

*stereoisomer with R configuration

EXAMPLE 71

Preparation of (S)-1-phenyl-1-(tert-butoxycarbonylamino)-2-N-cyano-N-(indoline-5-sulfonyl)aminoethane (10, $R_1$=Ph)

(S)-1-Phenyl-1-(tert-butoxycarbonylamino)-2-N-cyano-N-(1-trifluoroacetylindoline-5-sulfonyl)aminoethane from Example 2 (1.03 g, 0.002 mol) was suspended in 15 mL MeOH and 1.5 mL triethylamine and gently heated with stirring until the solid was completely dissolved. Reaction mixture was then stirred at room temperature for 6 hrs. White precipitate was collected by filtration, washed with water and dried, affording 726 mg of the title compound. Yield: 82%; $(MH)^+$=443.

EXAMPLE 72

Preparation of (S)-4-phenyl-1-[(imidazo-1-carbonyl)-indoline-5-sulfonyl]-3-tert-butoxycarbonyl-4,5-dihydro-1H-imidazol-2-imine (11, $R_1$=Ph, $R_3$=1-methyl-1H-pyrrol-2-yl)

A mixture of (S)-1-phenyl-1-(tert-butoxycarbonylamino)-2-N-cyano-N-(indoline-5-sulfonyl)aminoethane (2.215 g, 0.005 mol), 25 mL of tetrahydrofuran, 2.0 mL triethylamine and 1,1-carbonyldiimidazole (2.45 g, 0.015 mol) was stirred at 65° C. for 36 hrs. After cooling the reaction mixture was diluted with dichloromethane (100 mL) and shaken with water (2×100 mL). Organic layer was separated, dried and evaporated. Crude material was chromatographed on flash silica gel column using ethyl acetate to afford 2.175 g of title compound. Yield: 81%; $(MH)^+$=538.

EXAMPLE 73

Preparation of (S)-4-phenyl-1-[(3-dimethylaminopropylamino)-carbonylindoline-5-sulfonyl]-4,5-dihydro-1H-imidazol-2-amine dihydrochloride A mixture of (S)-4-phenyl-1-[(imidazo-1-carbonyl)-indoline-5-sulfonyl]-3-tert-butoxycarbonyl-4,5-dihydro-1H-imidazol-2-imine (270 mg, 0.5 mmol), 3 mL of dimethylaminoformamide and 1.5 mL of dimethylaminopropylamine was stirred at 80° C. for 1 hr. Solvent and the excess of amine were evaporated. The residue was dissolved in dichloromethane (4 mL) and stirred with trifluoroacetic acid (4 mL) for 1 hr at room temperature. Solvents were evaporated and the residue was purified by preparative HPLC using a gradient of 0.1% formic acid water solution—acetonitrile. Fractions containing the desired product were made basic and extracted with dichloromethane. The extract was dried, acidified with 1 N HCl in ether and evaporated. Crude product was dissolved in water and lyophilized to give 139 mg of the title compound. Yield: 51%; $(MH)^+$=471.

EXAMPLES 74-110

The following compounds are made using the methods described and exemplified above. All compounds presented in the table below provided NMR spectra consistent with their structures, and correct parent ion signals corresponding to their molecular weights when characterized by mass spectrometry run in the ESI mode.

| Example | $R_1$ | $R_3$ |
|---|---|---|
| 74 | Ph | $N(CH_3)CH_2CH_2CH_2N(CH_3)_2$ |
| 75 | Ph | $NHCH_2CH_2OCH_3$ |
| 76 | H | $NHCH_2CH_2OCH_3$ |
| 77 | Ph | $NHCH_2CH_2NH_2$ |
| 78 | H | $NHCH_2CH_2NH_2$ |
| 79 | Ph | HN—[4-(N-benzyl)piperidinyl-Ph] |
| 80 | iso-$C_3H_7$ | $NHCH_2CH_2CH_2N(CH_3)_2$ |
| 81 | cyclohexyl | $NHCH_2CH_2CH_2N(CH_3)_2$ |
| 82 | Ph | $NHCH_2CH_2CH_3$ |
| 83 | 4-F—$C_6H_4$— | $NHCH_2CH_2CH_3$ |
| 84 | 4-$CH_3O$—$C_6H_4$— | $NHCH_2CH_2CH_3$ |
| 85 | 3-Cl—$C_6H_4$— | $NHCH_2CH_2CH_3$ |
| 86 | 3-$CH_3$—$C_6H_4$— | $NHCH_2CH_2CH_3$ |
| 87 | 2-$CH_3$—$C_6H_4$— | $NHCH_2CH_2CH_3$ |
| 88 | 2-Cl—$C_6H_4$— | $NHCH_2CH_2CH_3$ |
| 89 | Ph | $NHCH_2CH_2CH_2CH_3$ |
| 90 | H | $NHCH_2CH_2CH_2CH_3$ |
| 91 | 4-F—$C_6H_4$— | $NHCH_2CH_2CH_2CH_3$ |
| 92 | 4-$CH_3O$—$C_6H_4$— | $NHCH_2CH_2CH_2CH_3$ |
| 93 | 3-Cl—$C_6H_4$— | $NHCH_2CH_2CH_2CH_3$ |
| 94 | 3-$CH_3$—$C_6H_4$— | $NHCH_2CH_2CH_2CH_3$ |
| 95 | 2-$CH_3$—$C_6H_4$— | $NHCH_2CH_2CH_2CH_3$ |
| 96 | 2-Cl—$C_6H_4$— | $NHCH_2CH_2CH_2CH_3$ |
| 97 | 4-Cl—$C_6H_4$— | $NHCH_2CH_2CH_2CH_3$ |
| 98 | Ph | $NHCH(CH_3)_2$ |
| 99 | Ph | NH-cyclo-$C_3H_5$ |
| 100 | Ph | $NHCH_2$-cyclo-$C_3H_5$ |
| 101 | Ph | $NHCH_2CH_2$-cyclo-$C_3H_5$ |
| 102 | Ph | $NHCH_2C(CH_3)_3$ |
| 103 | Ph | $NHC(CH_3)_3$ |
| 104 | Ph | $NHCH_2CH(CH_3)_2$ |
| 105 | 2-Me—$C_6H_4$— | NH-cyclo-$C_3H_5$ |
| 106 | 2-Me—$C_6H_4$— | $NHCH_2$-cyclo-$C_3H_5$ |
| 107 | 2-Me—$C_6H_4$— | $NHCH_2CH_2$-cyclo-$C_3H_5$ |
| 108 | 2-Me—$C_6H_4$— | $NHCH_2C(CH_3)_3$ |
| 109 | 2-Me—$C_6H_4$— | $NHC(CH_3)_3$ |
| 110 | 2-Me—$C_6H_4$— | $NHCH_2CH(CH_3)_2$ |

While the examples presented above describe a number of embodiments of this invention, it is apparent to those skilled in the relevant arts that the compounds, compositions, and methods of this invention can be altered to provide alternative embodiments, and equivalent compositions and methods.

EXAMPLE 111

Cell growth inhibitory activity of compounds of this invention was determined using a standard MTT assay. Adherent cells of colon human tumor (HT-29) sourced from ATCC (cells number: HTB-38) were treated with DMSO solutions of tested compounds with the ultimate concentration of DMSO in the test solution being 0.1%. Following the 72 hour long treatment MTT was added, and after a brief incubation the resulting formazan was dissolved in addional DMSO and the solutions were scanned using 570 nm wavelength.

The inhibitory activities of selected compounds are presented in the table below.

| Example | IC$_{50}$ range * |
|---------|-------------------|
| 35 | A |
| 36 | A |
| 37 | A |
| 38 | A |
| 39 | B |
| 40 | A |
| 41 | A |
| 42 | A |
| 43 | A |
| 44 | A |
| 44 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | C |
| 62 | C |
| 64 | A |
| 65 | B |
| 70 | A |
| 76 | B |
| 82 | A |
| 83 | A |
| 84 | B |
| 87 | A |
| 89 | A |
| 93 | A |
| 95 | A |
| 97 | B |
| 98 | A |
| 100 | A |
| 102 | A |

* MTT assay after 72 hr exposure to a tested compound. Ranges of cell growth inhibitory activities are defined as follows:
A: <100 nM,
B: 100-500 nM,
C: >500 nM.

We claim:

1. A compound having a structure according to Formula (I),

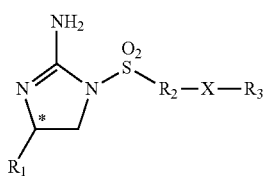

Formula I wherein:
R$_1$ is
a substituted or unsubstituted alkyl; or
a substituted or unsubstituted aryl or heteroaryl;
in either S or R configuration;
R$_2$ is
(a) a substituted or unsubstituted alkyl;
(b) a substituted or unsubstituted phenyl;
(c) a 5- or 6-membered, optionally substituted, saturated or unsaturated heterocyclic group having from one to three heteroatoms selected from nitrogen, oxygen and sulfur;
(d) a saturated or unsaturated fused ring carbocyclic group, optionally substituted, having from 8 to 10 ring atoms;
(e) a saturated or unsaturated fused ring heterocyclic group, optionally substituted, having from 8 to 10 ring atoms including one to three heteroatoms selected from nitrogen, oxygen and sulfur;
X is a hydrogen atom, carbonyl, thiocarbonyl or imine,
If X is a hydrogen atom then R$_3$ is null,
If X is not hydrogen then R$_3$ is:
(a) a substituted or unsubstituted linear, branched or cyclic alkyl which additionally can be connected to an aromatic or heterocyclic moiety,
(b) a substituted or unsubstituted phenyl,
(c) a 5- or 6-membered, saturated or unsaturated heterocyclic group, optionally substituted, having from one to three heteroatoms selected from nitrogen, oxygen and sulfur;
(d) NR'(CH$_2$)$_n$R" where
R' is hydrogen or alkyl,
n is 0-3,
R" is unsubstituted or substituted alkyl, cycloalkyl, phenyl, benzyl, a 5- or 6-membered, optionally substituted saturated or unsaturated heterocyclic group having from one to three heteroatoms selected from nitrogen, oxygen and sulfur, and
R' and R" can be connected or not,
(e) O(CH$_2$)$_n$R" or S(CH$_2$)$_n$R" where R" and n are as defined above,
or a tautomer, pharmaceutically acceptable salt, hydrate, or solvate thereof.

2. A compound according to claim 1, wherein R$_1$ is unsubstituted or substituted alkyl, cycloalkyl, aryl, benzyl, 5- or 6-membered heterocycle, saturated or unsaturated heterocyclic group having from one to three heteroatoms selected from nitrogen, oxygen and sulfur, with all of them optionally having 1-3 substituents selected from halo, alkyl, alkenyl, alkynyl, hydroxy, amino and alkoxy groups.

3. A compound according to claim 1, wherein R$_1$ is attached to the 4,5-dihydro-1H-imidazole ring with S stereochemistry.

4. A compound according to claim 3, wherein R$_1$ is phenyl optionally substituted with lower alkyl, halide or alkoxy groups.

5. A compound according to claim 1, wherein R$_2$ is a heterocyclic moiety having more than 6 carbon atoms and one or more nitrogen, sulfur and/or oxygen atoms; the moieties may contain the atoms in a single ring or in fused rings and may be saturated or unsaturated and additionally substituted with amino or carboxy groups.

6. A compound according to claim 5, wherein R$_2$ is indolyl, quinolyl, chromanyl, benzimidazolyl, benzoxazolyl, benzothienyl, benzofuranyl, or quinolinyl.

7. A compound according to claim 5, wherein R$_2$ is indolinyl and X represents carbonyl moiety attached at position 1.

8. A compound according to claim 1, wherein R$_3$ is unsubstituted or substituted alkyl, heteroalkyl, aryl, benzyl, 5- or 6-membered heterocycle, saturated or unsaturated heterocyclic group having from one to three heteroatoms selected from nitrogen, oxygen and sulfur, with all of them optionally having 1-3 substituents selected from halo, alkyl, alkenyl, alkynyl, hydroxy, amino and alkoxy groups.

9. A compound according to claim 1, wherein R$_3$ is:
a. alkoxy, alkylthio, aryloxy or arylthio group optionally having 1-3 substituents selected from halo, alkyl, alkenyl, alkynyl, hydroxy, amino and alkoxy groups.
b. NR'(CH$_2$)$_n$R" wherein R' is hydrogen or alkyl; n is 0-3; R" is hydroxy or amino group, unsubstituted or substituted alkyl, phenyl, benzyl, a 5- or 6-membered, optionally substituted saturated or unsaturated heterocyclic group having from one to three heteroatoms selected from nitrogen, oxygen and sulfur, and R' and R" can be connected or not.

10. A compound according to claim 1, wherein $R_3$ is $NH(CH_2)_nR'''$; n is 0-3;
R''' is lower alkyl, branched lower alkyl or cycloalkyl ring containing 3-7 carbon atoms.

11. A compound according to claim 1, selected from the group consisting of:
(S)-4-phenyl-1-(phenylsulfonyl)-4,5-dihydro-1H-imidazol-2-amine,
(S)-4-phenyl-1-(4-N-methylamino-phenylsulfonyl)-4,5-dihydro-1H-imidazol-2-amine,
(S)-4-phenyl-1-(4-N-acetyl-N-methylamino)-phenylsulfonyl-4,5-dihydro-1H-imidazol-2-amine,
(S)-4-phenyl-1-[4-(2-furanoylamino)-phenylsulfonyl]-4,5-dihydro-1H-imidazol-2-amine,
(S)-4-phenyl-1-[4-(1-pyrrolidin-2-onyl)-phenylsulfonyl]-4,5-dihydro-1H-imidazol-2-amine, and
(S)-4-phenyl-1-[4-(1-pyrrolidine-2,5-dionyl)-phenylsulfonyl]-4,5-dihydro-1H-imidazol-2-amine, or a tautomer, pharmaceutically acceptable salt, hydrate, or solvate thereof.

12. A compound according to claim 1, selected from the group consisting of:
(S)-4-phenyl-1-((N-1-methyl-1H-pyrrol-2-yloyl)indoline-5-sulfonyl)-4,5-dihydro-1H-imidazol-2-amine,
(S)-4-phenyl-1-(furan-2-yloylindoline-5-sulfonyl)-4,5-dihydro-1H-imidazol-2-amine,
(S)-(5-(2-amino-4-isopropyl-4,5-dihydro-1H-imidazol-1-ylsulfonyl)indolin-1-yl)(furan-2-yl) methanone,
(S)-(5-(2-amino-4-cyclohexyl-4,5-dihydro-1H-imidazol-1-ylsulfonyl)indolin-1-yl)(furan-2-y) methanone,
(S)-4-phenyl-1-(thiophene-2-yloylindoline-5-sulfonyl)-4,5-dihydro-1H-imidazol-2-amine,
(S)-4-phenyl-1-(acetylindoline-5-sulfonyl)-4,5-dihydro-1H-imidazol-2-amine,
(S)-4-phenyl-1-(propionylindoline-5-sulfonyl)-4,5-dihydro-1H-imidazol-2-amine,
(S)-4-phenyl-1-(butyrylindoline-5-sulfonyl)-4,5-dihydro-1H-imidazol-2-amine,
(S)-4-phenyl-1-(isobutyrylindoline-5-sulfonyl)-4,5-dihydro-1H-imidazol-2-amine,
(S)-4-phenyl-1-(thiophen-2-ylacetylindoline-5-sulfonyl)-4,5-dihydro-1H-imidazol-2-amine,
(S)-4-phenyl-1-(benzoylindoline-5-sulfonyl)-4,5-dihydro-1H-imidazol-2-amine,
(S)-4-phenyl-1-(4-nitrobenzoylindoline-5-sulfonyl)-4,5-dihydro-1H-imidazol-2-amine,
(S)-4-phenyl-1-[(4-dimethylaminobenzoyl)-indoline-5-sulfonyl]-4,5-dihydro-1H-imidazol-2-amine,
(S)-4-phenyl-1-(4-ethoxybenzoylindoline-5-sulfonyl)-4,5-dihydro-1H-imidazol-2-amine,
(S)-4-phenyl-1-(phenylacetylindoline-5-sulfonyl)-4,5-dihydro-1H-imidazol-2-amine,
(S)-4-phenyl-1-(methoxycarbonylindoline-5-sulfonyl)-4,5-dihydro-1H-imidazol-2-amine,
(S)-4-phenyl-1-[(1-acetyl-piperidin-4-yloyl)-indoline-5-sulfonyl]-4,5-dihydro-1H-imidazol-2-amine,
(S)-4-phenyl-1-(cyclohexanyloyl-indoline-5-sulfonyl)-4,5-dihydro-1H-imidazol-2-amine,
(S)-4-phenyl-1-[(naphthalen-4-yloyl)-indoline-5-sulfonyl]-4,5-dihydro-1H-imidazol-2-amine,
(S)-4-phenyl-1-[(pyridin-3-yloyl)-indoline-5-sulfonyl]-4,5-dihydro-1H-imidazol-2-amine,
(S)-4-phenyl-1-[(4-aminobenzoyl)-2-methylindoline-5-sulfonyl]-4,5-dihydro-1H-imidazol-2-amine,
(S)-4-phenyl-1-[(isopropylaminothiocarbonyl)-indoline-5-sulfonyl]-4,5-dihydro-1H-imidazol-2-amine,
(S)-4-phenyl-1-[1-butanoyl-3,4-dihydroquinoline-5-sulfonyl]-4,5-dihydro-1H-imidazol-2-amine,
(R)-4-phenyl-1-[1-butanoylindoline-5-sulfonyl]-4,5-dihydro-1H-imidazol-2-amine,
(S)-4-(4-fluorophenyl)-1-(furan-2-yloylindoline-5-sulfonyl)-4,5-dihydro-1H-imidazol-2-amine,
(S)-4-(4-fluorophenyl)-1-((1-methyl-1H-pyrrol-2-yl)indoline-5-sulfonyl)-4,5-dihydro-1H-imidazol-2-amine,
(S)-4-(2,4-difluorophenyl)-1-((1-methyl-1H-pyrrol-2-yl)indoline-5-sulfonyl)-4,5-dihydro-1H-imidazol-2-amine,
(S)-4-(4-chlorophenyl)-1-((1-methyl-1H-pyrrol-2-yl)indoline-5-sulfonyl)-4,5-dihydro-1H-imidazol-2-amine,
(S)-4-(4-methoxyphenyl)-1-((1-methyl-1H-pyrrol-2-yl)indoline-5-sulfonyl)-4,5-dihydro-1H-imidazol-2-amine,
(S)-4-(3-chlorophenyl)-1-((1-methyl-1H-pyrrol-2-yl)indoline-5-sulfonyl)-4,5-dihydro-1H-imidazol-2-amine,
(S)-4-(2-chlorophenyl)-1-((1-methyl-1H-pyrrol-2-yl)indoline-5-sulfonyl)-4,5-dihydro-1H-imidazol-2-amine,
(S)-4-(3-methylphenyl)-1-((1-methyl-1H-pyrrol-2-yl)indoline-5-sulfonyl)-4,5-dihydro-1H-imidazol-2-amine,
(S)-4-(2-methylphenyl)-1-((1-methyl-1H-pyrrol-2-yl)indoline-5-sulfonyl)-4,5-dihydro-1H-imidazol-2-amine,
(S)-4-methyl-1-((1-methyl-1H-pyrrol-2-yl)indoline-5-sulfonyl)-4,5-dihydro-1H-imidazol-2-amine,
(S)-4-(3,5-dichlorophenyl)-1-((1-methyl-1H-pyrrol-2-yl)indoline-5-sulfonyl)-4,5-dihydro-1H-imidazol-2-amine,
(S)-4-(pyrimidin-2-yl)-1-((1-methyl-1H-pyrrol-2-yl)indoline-5-sulfonyl)-4,5-dihydro-1H-imidazol-2-amine,
(S)-1-(indolin-5-ylsulfonyl)-4-phenyl-4,5-dihydro-1H-imidazol-2-amine
(S)-4-phenyl-1-[(3-dimethylaminopropylamino)-carbonylindoline-5-sulfonyl]-4,5-dihydro-1H-imidazol-2-amine,
(S)-4-phenyl-1-[(3-dimethylaminopropyl-methylamino)-carbonylindoline-5-sulfonyl]-4,5-dihydro-1H-imidazol-2-amine,
(S)-4-phenyl-1-[(2-methoxyethanamino)-carbonylindoline-5-sulfonyl]-4,5-dihydro-1H-imidazol-2-amine,
(S)-4-phenyl-1-[(2-aminoethylamino)-carbonylindoline-5-sulfonyl]-4,5-dihydro-1H-imidazol-2-amine,
(S)-4-phenyl-1-[(1-benzylpiperidin-4-ylamino)carbonylindoline-5-sulfonyl]-4,5-dihydro-1H-imidazol-2-amine,
(S)-4-isopropyl-1-[(3-dimethylaminopropylamino)-carbonylindoline-5-sulfonyl]-4,5--dihydro-1H-imidazol-2-amine,
(S)-4-cyclohexyl-1-[(3-dimethylaminopropylamino)-carbonylindoline-5-sulfonyl]-4,5-dihydro-1H-imidazol-2-amine,
(S)-4-phenyl-1-[(1-propylaminocarbonyl)indoline-5-sulfonyl]-4,5-dihydro-1H-imidazol-2-amine,
(S)-4-(4-fluorophenyl)-1-[(1-propylaminocarbony)indoline-5-sulfonyl]-4,5-dihydro-1H-imidazol-2-amine,
(S)-4-(4-methoxyphenyl)-1-[(1-propylaminocarbony)indoline-5-sulfonyl]-4,5-dihydro-1H-imidazol-2-amine,
(S)-4-(3-chlorophenyl)-1-[(1-propylaminocarbonyl)indoline-5-sulfonyl]-4,5-dihydro-1H-imidazol-2-amine,
(S)-4-(3-methylphenyl)-1-[(1-propylaminocarbonyl)indoline-5-sulfonyl]-4,5-dihydro-1H-imidazol-2-amine, (S)-4-(2-methylphenyl)-1-[(1-propylaminocarbonyl)indoline-5-sulfonyl]-4,5-dihydro-1H-imidazol-2-amine,
(S)-4-(2-chlorophenyl)-1-[(1-propylaminocarbonyl)indoline-5-sulfonyl]-4,5-dihydro-1H-imidazol-2-amine,
(S)-4-phenyl-1-[(1-butylaminocarbonyl)indoline-5-sulfonyl]-4,5-dihydro-1H-imidazol-2-amine,
(S)-4-(4-fluorophenyl)-1-[(1-butylaminocarbonyl)indoline-5-sulfonyl]-4,5-dihydro-1H-imidazol-2-amine,
(S)-4-(4-methoxyphenyl)-1-[(1-butylaminocarbony)indoline-5-sulfonyl]-4,5-dihydro-1H-imidazol-2-amine,
(S)-4-(3-chlorophenyl)-1-[(1-butylaminocarbonyl)indoline-5-sulfonyl]-4,5-dihydro-1H-imidazol-2-amine,
(S)-4-(3-methylphenyl)-1-[(1-butylaminocarbonyl)indoline-5-sulfonyl]-4,5-dihydro-1H-imidazol-2-amine,
(S)-4-(2-methylphenyl)-1-[(1-butylaminocarbonyl)indoline-5-sulfonyl]-4,5-dihydro-1H-imidazol-2-amine,
(S)-4-(2-chlorophenyl)-1-[(1-butylaminocarbonyl)indoline-5-sulfonyl]-4,5-dihydro-1H-imidazol-2-amine,
(S)-4-(4-chlorophenyl)-1-[(1-butylaminocarbonyl)indoline-5-sulfonyl]-4,5-dihydro-1H-imidazol-2-amine,
(S)-4-phenyl-1-[(isopropylaminocarbonyl)indoline-5-sulfonyl]-4,5-dihydro-1H-imidazol-2-amine,
(S)-4-phenyl-1-[(cyclopropylaminocarbonyl)indoline-5-sulfonyl]-4,5-dihydro-1H-imidazol-2-amine,
(S)-4-phenyl-1-[((cyclopropylmetyl)aminocarbonyl)indoline-5-sulfonyl]-4,5-dihydro-1H-imidazol-2-amine,
(S)-4-phenyl-1-[((cyclopropylethyl)aminocarbonyl)indoline-5-sulfonyl]-4,5-dihydro-1H-imidazol-2-amine,
(S)-4-phenyl-1-[(isobutylaminocarbonyl)indoline-5-sulfonyl]-4,5-dihydro-1H-imidazol-2-amine,
(S)-4-phenyl-1-[(tert-butylaminocarbony)indoline-5-sulfonyl]-4,5-dihydro-1H-imidazol-2-amine,
(S)-4-phenyl-1-[(neopentylaminocarbony)indoline-5-sulfonyl]-4,5-dihydro-1H-imidazol-2-amine,
(S)-4-(2-methylphenyl)-1-[(cyclopropylaminocarbonyl)indoline-5-sulfonyl]-4,5-dihydro-1H-imidazol-2-amine,
(S)-4-(2-methylphenyl)-1-[((cyclopropylmetyl)aminocarbonyl)indoline-5-sulfonyl]-4,5-dihydro-1H-imidazol-2-amine,
(S)-4-(2-methylphenyl)-1-[((cyclopropylethyl)aminocarbonyl)indoline-5-sulfonyl]-4,5-dihydro-1H-imidazol-2-amine,
(S)-4-(2-methylphenyl)-1-[(neopentylaminocarbonyl)indoline-5-sulfonyl]-4,5-dihydro-1H-imidazol-2-amine,
(S)-4-(2-methylphenyl)-1-[(tert-butylaminocarbonyl)indoline-5-sulfonyl]-4,5-dihydro-1H-imidazol-2-amine, and
(S)-4-(2-methylphenyl)-1-[(isobutylaminocarbonyl)indoline-5-sulfonyl]-4,5-dihydro-1H-imidazol-2-amine,
or a tautomer, pharmaceutically acceptable salt, hydrate, or solvate thereof.

13. A pharmaceutical composition comprising a therapeutically effective amount of a compound of claim 1, or a tautomer, pharmaceutically acceptable salt, hydrate, or solvate thereof, together with a pharmaceutically acceptable carrier.

14. A pharmaceutical composition comprising a compound of claim 1, its salt, hydrate, or solvate thereof, together with a pharmaceutically acceptable carrier and an anti-cancer agent.

15. A compound selected from the following:
1-(phenylsulfonyl)-4,5-dihydro-1H-imidazol-2-amine;
1-[(2-methoxyethanamino)-carbonylindoline-5-sulfonyl]-4,5-dihydro-1H-imidazol-2-amine;
1-[(2-aminoethylamino)-carbonylindoline-5-sulfonyl]-4,5-dihydro-1H-imidazol-2-amine; and
1-[(1-butylaminocarbonyl)indoline-5-sulfonyl]-4,5-dihydro-1H-imidazol-2-amine.

* * * * *

UNITED STATES PATENT AND TRADEMARK OFFICE
CERTIFICATE OF CORRECTION

PATENT NO.        : 8,981,114 B2
APPLICATION NO.   : 14/307272
DATED             : March 17, 2015
INVENTOR(S)       : Stanislaw Wieslaw Pikul et al.

Page 1 of 1

It is certified that error appears in the above-identified patent and that said Letters Patent is hereby corrected as shown below:

Title Page Item (71):
"OncoArendi Therapeutics Sp. z.o.o, Warsaw (PL)" should read, --OncoArendi Therapeutics Sp. z.o.o., Warszawa (PL)--.

In the Claims

Column 17, Lines 34-35:
"(S)-(5-(2-amino-4-cyclohexyl-4,5-dihydro-1H-imidazol-1-ylsulfonyl)indolin-1-yl)(furan-2-y)methanone," should read, --(S)-(5-(2-amino-4-cyclohexyl-4,5-dihydro-1H-imidazol-1-ylsulfonyl)indolin-1-yl)(furan-2-yl)methanone,--.

Signed and Sealed this
First Day of March, 2016

Michelle K. Lee
*Director of the United States Patent and Trademark Office*